US010398315B2

(12) United States Patent
Olivo et al.

(10) Patent No.: US 10,398,315 B2
(45) Date of Patent: Sep. 3, 2019

(54) METHOD OF IMAGING LIVING TISSUE

(71) Applicant: Agency for Science, Technology and Research, Singapore (SG)

(72) Inventors: Malini Olivo, Singapore (SG); Jun Hui Ho, Singapore (SG); Dinish Unnimadhava Kurup Soudamini Amma, Singapore (SG); Chi Lok Wong, Singapore (SG); Ghayathri Balasundaram, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 314 days.

(21) Appl. No.: 15/038,029

(22) PCT Filed: Dec. 8, 2014

(86) PCT No.: PCT/SG2014/000585
§ 371 (c)(1),
(2) Date: May 19, 2016

(87) PCT Pub. No.: WO2015/084270
PCT Pub. Date: Jun. 11, 2015

(65) Prior Publication Data
US 2016/0310010 A1 Oct. 27, 2016

(30) Foreign Application Priority Data
Dec. 6, 2013 (SG) .................................. 201309067

(51) Int. Cl.
*A61B 5/00* (2006.01)
*A61B 8/08* (2006.01)
*A61K 49/00* (2006.01)
*A61K 49/22* (2006.01)
*G01N 33/483* (2006.01)

(52) U.S. Cl.
CPC ............ *A61B 5/0095* (2013.01); *A61B 8/481* (2013.01); *A61K 49/003* (2013.01); *A61K 49/0036* (2013.01); *A61K 49/0093* (2013.01); *A61K 49/22* (2013.01); *G01N 33/4833* (2013.01)

(58) Field of Classification Search
CPC .... A61B 5/0095; A61B 8/481; A61K 49/003; A61K 49/0036; A61K 49/0093; A61K 49/22; G01N 33/4833
See application file for complete search history.

(56) References Cited

U.S. PATENT DOCUMENTS

| 6,123,923 A | 9/2000 | Unger et al. |
| 6,183,727 B1 | 2/2001 | Gust, Jr. et al. |
| 2011/0081294 A1 | 4/2011 | Fukui et al. |
| 2012/0165646 A1 | 6/2012 | Yamauchi et al. |
| 2012/0296192 A1* | 11/2012 | Fukutani ............... A61B 5/0095 600/407 |
| 2014/0140959 A1* | 5/2014 | Szalay ................. A61K 49/006 424/93.2 |
| 2015/0272444 A1* | 10/2015 | Maslov ................ A61B 5/0095 600/407 |

FOREIGN PATENT DOCUMENTS

| EP | 0906758 B1 | 4/2011 |
| WO | 9857667 A1 | 12/1998 |
| WO | 2010009747 A1 | 1/2010 |
| WO | 2011044671 A1 | 4/2011 |

OTHER PUBLICATIONS

International Preliminary Report on Patentability for International Application No. PCT/SG2014/000585 dated Apr. 5, 2016, pp. 1-14.
extended European Search Report issued by European Patent Office for European Patent Application No. 14 868 398.0 dated May 2, 2017, pp. 1-12.
Xiang et al., "Pulse Laser Integrated Photodynamic Therapy and Photoacoustic Imaging," Photons Plus Ultrasound: Imaging and Sensing 2007: The Eighth Conference on Biomedical Thermoacoustics, Optoacoustics and Acousto-optics, Proc. of SPIE, vol. 6437, 2007, pp. 1-8.
Lovell et al., "Activatable Photosensitizers for Imaging and Therapy," Chem. Rev., vol. 110, 2010, pp. 2839-2857.
Kamat et al., "Excited-State Properties and Photosensitization Behaviour of Bis(2,4-Dihydroxyphenyl) Squaraine," J. Chem. Soc., Faraday Trans., vol. 89, No. 14, 1993, pp. 2397-2402.
Yano et al., "Current States and Future Views in Photodynamic Therapy," Journal of Photochemistry and Photobiology C: Photochemistry Reviews, vol. 12, 2011, pp. 46-67.
Van Leengoed et al., "In Vivo Fluorescence and Photodynamic Activity of Zinc Phthalocyanine Administered in Liposomes," Br. J. Cancer, vol. 69, 1994, pp. 840-845.
Koo et al., "In Vivo Tumor Diagnosis and Photodynamic Therapy via Tumoral pH-Responsive Polymeric Micelles," Chem. Commun., vol. 46, No. 31, 2010, pp. 5668-5670.
Avirah et al., "Squaraine Dyes in PDT: From Basic Design to in Vivo Demonstration," Organic & Biomolecular Chemistry, vol. 10, 2012, pp. 911-920.
Shim et al., "Enhanced Tumor Localization and Retention of Chlorin e6 in Cationic Nanolipoplexes Potentiate the Tumor Ablation Effects of Photodynamic Therapy," Nanotechnology, vol. 22, 2011, 365101 pp. 1-8.
Chen et al., "Apoptosis Induced by Methylene-Blue-Mediated Photodynamic Therapy in Melanomas and the Involvement of Mitochondrial Dysfunction Revealed by Proteomics," Cancer Sci., vol. 99, No. 10, Oct. 2008, pp. 2019-2027.

(Continued)

*Primary Examiner* — Ruth S Smith
(74) *Attorney, Agent, or Firm* — Winstead, P.C.

(57) ABSTRACT

A method of imaging living tissue is provided. The method includes introducing a photoacoustic contrast agent comprising or consisting of a photosensitizer into living tissue; and obtaining an image of the living tissue by photoacoustic imaging. Use of a photoacoustic contrast agent comprising or consisting of a photosensitizer in photoacoustic imaging is also provided.

6 Claims, 14 Drawing Sheets

(56) References Cited

OTHER PUBLICATIONS

Rosenthal et al., "Fast Semi-Analytical Model-Based Acoustic Inversion for Quantitative Optoacoustic Tomography," IEEE Trans. Med. Imag., vol. 29, 2010, pp. 1275-1285.
Yang et al., "Photoacoustic Tomography: In Vivo Imaging from Organelles to Organs," Science, vol. 335, 2012, pp. 1458-1462.
Lihong V. Wang, "Multiscale Photoacoustic Microscopy and Computed Tomography," Nat. Photonics, vol. 3, 2009, pp. 503-509.
Yao et al., "Photoacoustic Microscopy," Laser & Photonics Rev., vol. 7, No. 5, 2013, pp. 758-778.
Vakoc et al., "Innovation: Cancer Imaging by Optical Coherence Tomography: Preclinical Progress and Clinical Potential," Nat. Reviews Cancer, vol. 12, 2012, pp. 363-368.
Ku et al., "Imaging of Tumor Angiogenesis in Rat Brains in Vivo by Photoacoustic Tomography," Appl. Opt., vol. 44, No. 5, 2005, pp. 770-775.
Stein et al., "Noninvasive, in Vivo Imaging of Blood-Oxygenation Dynamics within the Mouse Brain Using Photoacoustic Microscopy," J. Biomed. Opt., vol. 14, No. 2, 020502, Mar./Apr. 2009, pp. 1-3.
Burton et al., "Multispectral Opto-acoustic Tomography (MSOT) of the Brain and Glioblastoma Characterization," NeuroImage, vol. 65, 2013, pp. 522-528.
Buehler et al., "Real-Time Handheld Multispectral Optoacoustic Imaging," Opt. Lett., vol. 38, No. 9, 2013, pp. 1404-1406.
Kruger et al., "Photoacoustic Angiography of the Breast," Med. Phys., vol. 37, No. 11, 2012, pp. 6096-6100.
Luke et al., "Biomedical Applications of Photoacoustic Imaging with Exogenous Contrast Agents," Ann. Biomed. Eng., vol. 40, No. 2, 2012, pp. 422-437.
Kircher et al, "A Brain Tumor Molecular Imaging Strategy Using a New Triple-Modality MRI-Photoacoustic-Raman Nanoparticle," Nat. Med., vol. 18, No. 5, 2012, pp. 829-834.
De La Zerda et al., "Family of Enhanced Photoacoustic Imaging Agents for High-Sensitivity and Multiplexing Studies in Mice," ACS Nano., vol. 6, No. 6, 2012, pp. 4694-4701.
De La Zerda et al., "Ultrahigh Sensitivity Carbon Nanotube Agents for Photoacoustic Molecular Imaging in Living Mice," Nano Lett., vol. 10, 2010, pp. 2168-2172.
De La Zerda et al., "Carbon Nanotubes as Photoacoustic Molecular Imaging Agents in Living Mice," Nat. Nanotech, vol. 3, 2008, pp. 557-562.
Buehler et al., "High Resolution Tumor Targeting in Living Mice by Means of Multispectral Optoacoustic Tomography," EJNIMMI Research, vol. 2, No. 14, 2012, pp. 1-6.
Taruttis et al., "Fast Multispectral Optoacoustic Tomography (MSOT) for Dynamic Imaging of Pharmacokinetics and Biodistribution in Multiple Organs," PLoS One, vol. 7, Issue 1, 2012, pp. 1-6.
Herzog et al, "Optical Imaging of Cancer Heterogeneity with Multispectral Optoacoustic Tomography," Radiology, vol. 263, No. 2, 2012, pp. 461-468.
Taruttis et al., "Real-Time Imaging of Cardiovascular Dynamics and Circulating Gold Nanorods with Multispectral Optoacoustic Tomography," Opt. Express, vol. 18, No. 19, 2010, pp. 19592-19602.
Yang et al., "Magnetic Gold-Nanorod/ PNIPAAmMA Nanoparticles for Dual Magnetic Resonance and Photoacoustic Imaging and Targeted Photothermal Therapy," Biomaterials, vol. 34, 2013, pp. 5651-5660.
Rouleau et al., "VCAM-1-Targeting Gold Nanoshell Probe for Photoacoustic Imaging of Atherosclerotic Plaque in Mice," Contrast Media Mol. Imag., vol. 8, 2013, pp. 27-39.
Nie et al., "In Vivo Volumetric Photoacoustic Molecular Angiography and Therapeutic Monitoring with Targeted Plasmonic Nanostars," Small, vol. 10, No. 8, 2014, pp. 1585-1593.
Niidome et al., "PEG-Modified Gold Nanorods with a Stealth Character for in Vivo Applications," Journal of Controlled Release, vol. 114, No. 3, 2006, pp. 343-347.
O'Connor et al., "Porphyrin and Nonporphyrin Photosensitizers in Oncology: Preclinical and Clinical Advances in Photodynamic Therapy," Photochemistry and Photobiology, vol. 85, 2009, pp. 1053-1074.
Abuteen et al., "The Evaluation of NIR-Absorbing Porphyrin Derivatives as Contrast Agents in Photoacoustic Imaging," Phys. Chem. Chem. Phys., vol. 15, 2013, pp. 18502-18509.
Greish, "Enhanced Permeability and Retention (EPR) Effect for Anticancer Nanomedicine Drug Targeting," Cancer Nanotech. Methods Mol. Biol., vol. 624, 2010, pp. 25-37.
Isele et al., "Pharmacokinetics and Body Distribution of Liposomal Zinc Phthalocyanine in Tumor-Bearing Mice: Influence of Aggregation State, Particle Size, and Composition," J. Pharm. Sci., vol. 84, No. 2, 1995, pp. 166-173.
Ines et al.,"Biodistribution of Phototherapeutic Properties of Zinc (II) 2, 9, 16, 23-Tetrakis (Methooxy) Phthalocyanine in Vivo," Photodiagnosis and Photodynamic Therapy, vol. 6, 2009, pp. 62-70.
Rosenthal et al., "Fast Semi-Analytical Model-Based Acoustic Inversion for Quantitative Optoacoustic Tomography," IEEE Trans. Med. Imag., vol. 29, No. 6, 2010, pp. 1275-1285.
Ho et al., "Multifunctional Photosensitizer-Based Contrast Agents for Photoacoustic Imaging," Scientific Reports, vol. 4, Article No. 5342, 2014, pp. 1-6.
Paul Beard, "Biomedical Photoacoustic Imaging," Interface Focus, vol. 1, No. 4, 2011, pp. 602-631.
Ma et al., "Multispectral Optoacoustic Tomography (MSOT) Scanner for Whole-Body Small Animal Imaging," Journal of Optics Express, vol. 17, No. 24, 2009, pp. 21414-21426.
Song et al., "Noninvasive Photoacoustic Identification of Sentinel Lymph Nodes Containing Methylene Blue in vivo in a Rat Model," J. Biomed. Opt. 2008, vol. 13, No. 5, pp. 1-13.

\* cited by examiner

METHOD OF IMAGING LIVING TISSUE

CROSS-REFERENCE TO RELATED APPLICATION

This application claims the benefit of priority of Singapore patent application No. 201309067-5 filed on 6 Dec. 2013, the content of which is incorporated herein by reference in its entirety for all purposes.

TECHNICAL FIELD

The invention relates to bioimaging.

BACKGROUND

Photoacoustic imaging (PAI) is a rapid emerging biomedical imaging modality which provides non-invasive, in vivo functional imaging information at clinically relevant penetration depths, while maintaining high spatial resolution and image contrast.

It generally involves flashing a laser at low energy onto a target area or region on a subject's body. The laser at low energy may penetrate deeply into the body to create a large radiated area for more detailed imaging. Rapid absorption of laser energy by endogenous chromophores such as hemoglobin and melanin, as well as exogenous contrast agents in tissue may expand the tissue through transient thermoelastic expansion. This expansion creates ultrasonic acoustic pressure waves that may be detected using ultrasound detectors of appropriate sensitivity, such as ultrasound transducers. The transducer readings may be processed and interpreted using mathematical algorithms to create two dimensional or three dimensional images of the target area to depict the tissue structure. The higher penetration depth of PA imaging (5 cm to 6 cm) over fluorescence and optical coherence tomography (OCT) enables deep tissue imaging, especially in clinical settings.

In terms of applications, endogenous hemoglobin in blood has been used for PA imaging of tumor vascular network in rat brain, blood-oxygenation dynamics in mouse brain, human arm, as well as breast imaging. In addition, various exogenous contrast agents, such as carbon nanotubes (SWNTs), near-infrared (NIR) dyes like indocyanine green (ICG), as well as gold nanoparticles, have been introduced to enhance imaging contrast.

Clinical application of these contrast agents, however, has been limited due to cytotoxicity issues. Even though attempts have been made to circumvent this problem, such as surface modification of gold nanorods with polyethylene glycol (PEG) to lower cytotoxicity and increase blood circulation time, there remains a need for improved methods for bioimaging.

In view of the above, there remains a need for methods of imaging living tissue that overcome or at least alleviate one or more of the above-mentioned problems.

SUMMARY

In a first aspect, a method of imaging living tissue is provided. The method comprises
 a) introducing a photoacoustic contrast agent comprising or consisting of a photosensitizer into living tissue; and
 b) obtaining an image of the living tissue by photoacoustic imaging.

In a second aspect, use of a photoacoustic contrast agent comprising or consisting of a photosensitizer in photoacoustic imaging is provided.

BRIEF DESCRIPTION OF THE DRAWINGS

The invention will be better understood with reference to the detailed description when considered in conjunction with the non-limiting examples and the accompanying drawings, in which.

DETAILED DESCRIPTION

Figure 1:
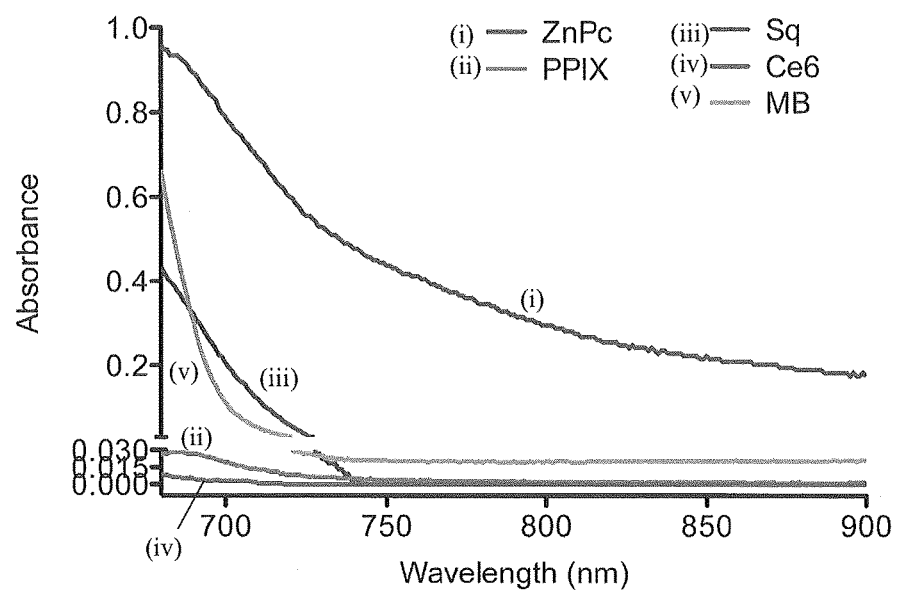
FIG. 1 is a graph showing normalized absorbance as a function of wavelength for five exemplary photosensitizers of zinc pthalocyanine (ZnPc), methylene blue (MB), 2,4-bis[4-(N,N-dibenzylamino)-2,6-dihydroxyphenyl]squaraine (Sq), protoporphyrin IX (PPIX), and chlorin e6 (Ce6) in the NIR region from 680 nm to 900 nm. ZnPc showed the highest overall absorbance, followed by MB, Sq, PPIX and Ce6, in decreasing order.

It has been demonstrated herein that various classes of photosensitizers may be used as contrast agents for photoacoustic imaging. Photosensitizers refer to light-absorbing photosensitive agents, and may encompass compounds used in photodynamic therapy (PDT). In their use in photodynamic therapy, the photosensitizers may accumulate selectively in certain target tissues. By irradiating the photosensitizers with electromagnetic radiation, reactive oxygen species such as singlet oxygen and/or free radicals may be produced in cells or other tissue containing the photosensitizers, such that oxidative damage from the reactive oxygen species are localized to target specific cells such as tumour cells, and lesions, so as to kill the specific cells and lesions. At the same time, the electromagnetic radiation is absorbed by the photosensitizers to result in local heating and thermoelastic expansion. The thermoelastic expansion may, in turn, produce megahertz ultrasonic waves in the material, thereby generating a photoacoustic signal, which may be used for photoacoustic imaging.

Most of the photosensitizers have high singlet oxygen quantum yields of about 0.5 and are able to offer high photodynamic therapy efficacy. They are however not suitable for use in high contrast diagnostic imaging such as fluorescent imaging due to their low fluorescence quantum yields of less than 0.2. Use of photosensitizers as contrast agents for photoacoustic imaging thus provides an attractive, alternative imaging technique due to their reasonably strong photoacoustic signals based on energy conservation between fluorescence and photoacoustics, exhibiting excellent multifunctional capabilities with high photoacoustic signals and high PDT efficacy. Advantageously, the photosensitizers are free from interference from photobleaching and autofluorescence, unlike that of conventional fluorescence imaging.

Moreover, use of multispectral optacoustic tomographic (MSOT) imaging allows detection of endogenous absorbers, such as oxygenated and deoxygenated hemoglobin, so that tumor blood vasculature and oxygenation status may be monitored at the same time. As disclosed herein, in vivo localization and biodistribution in a preclinical animal model of cancer, where preferential accumulation of photosensitizers in tumors due to enhanced permeation and retention (EPR) effect that enabled achievement of longitudinal monitoring of cancer, has been demonstrated.

With the above in mind, various embodiments disclosed herein refer to a method of imaging living tissue. The method includes introducing a photoacoustic contrast agent comprising or consisting of a photosensitizer into living tissue; and obtaining an image of the living tissue by photoacoustic imaging.

The term "photoacoustic imaging" as used herein refers to signal generation caused by an electromagnetic pulse, with absorption and expansion of a photoacoustic imaging contrast agent, followed by acoustic detection, where the photoacoustic imaging contrast agent absorbs the light energy and converts it to thermal energy that generates the photoacoustic signal. The terms "photoacoustic contrast agent" or "photoacoustic imaging contrast agent" are used interchangeably with the term "optoacoustic contrast agent", and refer generally to a compound used to enhance contrast of living tissue, to thereby improve visibility thereof when acquiring optical images by photoacoustic imaging. A contrast agent may be helpful in qualitatively and quantitatively determining disease and/or injury by improving visibility and contrast of an object of interest, such as living tissue, or internal body structures such as vessels or organs.

The photoacoustic contrast agent comprises or consists of a photosensitizer. As mentioned above, the term "photosensitizer" refers generally to light-absorbing photosensitive agents, and may encompass compounds used in photodynamic therapy. In its use in photodynamic therapy, the photosensitizer may accumulate selectively in certain target tissues. Upon irradiation with electromagnetic radiation, such as light of an appropriate wavelength, reactive oxygen species such as singlet oxygen and/or free radicals, which promotes cell damage or death, may be produced in cells or other tissue containing the photosensitizer. Oxidative damage from these reactive intermediates may be localized to the cells or structures at which the photosensitizer is present, hence in case the photosensitizer is present in significant quantity only at desired target sites, and/or light activation is performed only at such target sites, treatments involving use of the photosensitizer may be capable of targeting specific cells. Advantageously, photosensitizers are excellent photodynamic therapeutic agents and hence, suitable for cancer treatment.

As mentioned above, it has been demonstrated herein that various classes of photosensitizers may be used as contrast agents for photoacoustic imaging. Photosensitizers may generally be classified as a porphyrin-based photosensitizer or a non-porphyrin-based photosensitizer.

Porphyrin-based photosensitizer may refer to compounds produced in vivo in the synthesis of heme and other endogenously produced photoactivatable compounds including their photoproducts. Examples of porphyrin-based photosensitizers include, but are not limited to, porphyrin, reduced porphyrin such as chlorin, chlorophyll, chlorophyll derivatives such as phyropheophorbide, chlorin e6, chlorin p6 and purpurin 18, synthetic chlorin such as benzoporphyrin derivative and purpurin, bacteriochlorin such as bacteriochlorophyll derivative, synthetic bacteriochlorin, porphyrin isomer such as porphycence, heteroatom-fused porphyrin and inverted porphyrin, expanded porphyrin such as texaphyrin, and porphyrin analog such as phthalocyanine and naphthalocyanine.

The porphyrin-based photosensitizers may be further categorized as first, second, or third generation photosensitizers. Examples of first generation photosensitizers include hematoporphyrin derivative (HPD), porfimer sodium, and combinations thereof. Examples of second generation photosensitizers include 5-aminolevulinic acid (ALA), chlorin, chlorin e6, sodium chlorin p6, benzoporphyrin derivative (BPD), lutenium texaphyrin, purpurins, phthalocyanines, meso-tetro-(hydroxyphenyl)-chlorin (mTHPC), phthalocyanine-4, texaphyrins, bacteriochlorophyll, and combinations thereof. Examples of third generation photosensitizers include biologic conjugates such as antibody conjugates and/or liposome conjugates.

In various embodiments, the photosensitizer comprises or consists of a second generation porphyrin-based photosensitizer. In some embodiments, the second generation porphyrin-based photosensitizer is selected from the group consisting of protoporphyrin, chlorin, pthalocyanine, and combinations thereof.

Apart from the above-mentioned porphyrin-based photosensitizers, the photosensitizer may comprise or consist of a non-porphyrin-based photosensitizer. Examples of a non-porphyrin-based photosensitizer include, but are not limited to, hypericin, cationic dye such as rhodamine, psoralen, merocyanine 540, squarine, methylene blue, and combinations thereof. In some embodiments, the non-porphyrin-based photosensitizer is selected from the group consisting of squarine, methylene blue, and combinations thereof.

In various embodiments, the photosensitizer is selected from the group consisting of a second generation porphyrin-based photosensitizer, a non-porphyrin-based photosensitizer, and combinations thereof For example, the photosensitizer may be selected from the group consisting of zinc pthalocyanine, methylene blue, 2,4-bis [4-(N,N-dibenzylamino)-2,6-dihydroxyphenyl]squaraine, protoporphyrin IX, chlorin e6, and combinations thereof.

In specific embodiments, the photosensitizer comprises or consists of zinc pthalocyanine. Advantageously, zinc pthalocyanine was found to generate the strongest photoacoustic signal with highest relative photoacoustic quantum yield among the tested compounds.

The photosensitizer may be conjugated to targeting moieties and/or incorporated into drug delivery systems to improve targeting efficacy for better tumor localization. The photosensitizers may also be conjugated to gold (Au) nanoplaforms of matching localized surface plasmon resonance (LSPR) to achieve improved photoacoustic signal, as well as to demonstrate a combined photodynamic and photothermal therapeutic effect upon irradiation with specific light source.

In various embodiments, the photosensitizer is conjugated or attached to a bioactive agent. As used herein, the term "bioactive agent" is defined as those organic molecules having an effect in a biological system, whether such system is in vitro, in vivo, or in situ. Biologically active molecules may include, but are not limited to growth factors, cytokines, antiseptics, antibiotics, anti-inflammatory agents, analgesics, anesthetics, chemotherapeutic agents, clotting agents, metabolites, chemoattractants, hormones, steroids, and other drugs, or cell attachment molecules.

In various embodiments, the bioactive agent is a protein, an antibody, an antibody fragment, an antibody like molecules, or a drug.

For instance, the bioactive agent may be a proteinaceous molecule, such as an antibody, for example a monoclonal or polyclonal antibody, which immunologically binds to a target analyte at a specific determinant or epitope. The term "antibody" is used in the broadest sense and specifically covers monoclonal antibodies as well as antibody variants, fragments or antibody like molecules, such as for example, Fab, F(ab')$_2$, scFv, Fv diabodies and linear antibodies, so long as they exhibit the desired binding activity.

In some embodiments, the bioactive agent is a monoclonal antibody. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. The monoclonal antibodies may include "chimeric" antibodies and humanized antibodies. A "chimeric" antibody is a molecule in which different portions are derived from different animal species, such as those having a variable region derived from a murine mAb and a human immunoglobulin constant region.

In some embodiments, the bioactive molecule is a polyclonal antibody. "Polyclonal antibodies" refer to heterogeneous populations of antibody molecules derived from the sera of animals immunized with an antigen, or an antigenic functional derivative thereof. For the production of polyclonal antibodies, host animals such as rabbits, mice and goats, may be immunized by injection with an antigen or hapten-carrier conjugate optionally supplemented with adjuvants.

"Peptide" generally refers to a short chain of amino acids linked by peptide bonds. Typically peptides comprise amino acid chains of about 2-100, more typically about 4-50, and most commonly about 6-20 amino acids. "Polypeptide" generally refers to individual straight or branched chain sequences of amino acids that are typically longer than peptides. "Polypeptides" usually comprise at least about 20 to 1000 amino acids in length, more typically at least about 100 to 600 amino acids, and frequently at least about 200 to about 500 amino acids. Included are homo-polymers of one specific amino acid, such as for example, poly-lysine. "Proteins" include single polypeptides as well as complexes of multiple polypeptide chains, which may be the same or different.

Multiple chains in a protein may be characterized by secondary, tertiary and quaternary structure as well as the primary amino acid sequence structure, may be held together, for example, by disulfide bonds, and may include post-synthetic modifications such as, without limitation, glycosylation, phosphorylation, truncations or other processing.

Antibodies such as IgG proteins, for example, are typically comprised of four polypeptide chains (i.e., two heavy and two light chains) that are held together by disulfide bonds. Furthermore, proteins may include additional components such associated metals (e. g., iron, copper and sulfur), or other moieties. The definitions of peptides, polypeptides and proteins includes, without limitation, biologically active and inactive forms; denatured and native forms; as well as variant, modified, truncated, hybrid, and chimeric forms thereof In the context of the invention, the term "drug" generally means a therapeutic or pharmaceutical agent which may be included and/or mixed into the photoacoustic contrast agent, or conjugated or attached to the photo sensitizer comprised or consisted in the photoacoustic contrast agent.

Examples of a drug include, but are not limited to: antiproliferative/antimitotic agents including natural products such as vinca alkaloids (e.g. vinblastine, vincristine, and vinorelbine), paclitaxel, epidipodophyllotoxins (e.g. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiproliferative/antimitotic alkylating agents such as nitrogen mustards (such as mechlorethamine, cyclophosphamide and analogs, melphalan, chlorambucil), ethylenimines and methylmelamines (hexamethylmelamine and thiotepa), alkyl sulfonates-busulfan, nirosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine)); platinum coordination complexes (cisplatin, carboplatin), procarbazine, hydroxyurea, mitotane, amino glutethimide; hormones (e.g. estrogen); anticoagulants (heparin, synthetic heparin salts and other inhibitors of thrombin); fibrinolytic agents (such as tissue plasminogen activator, streptokinase and urokinase); antiplatelet (such as aspirin, dipyridamole, ticlopidine, clopidogrel, abciximab); antimigratory; antisecretory (such as breveldin); antiinflammatory: such as adrenocortical steroids (Cortisol, cortisone, fludrocortisone, prednisone, prednisolone, 6-alpha-methylprednisolone, triamcinolone, betamethasone, and dexamethasone), non-steroidal agents (such as salicylic acid derivatives e.g. aspirin); para-aminophenol derivatives (e.g. acetaminophen); indole and indene acetic acids (such as indomethacin, sulindac, and etodalac), heteroaryl acetic acids (such as tolmetin, diclofenac, and ketorolac), arylpropionic acids (such as ibuprofen and derivatives), anthranilic acids (such as mefenamic acid, and meclofenamic acid), enolic acids (such as piroxicam, tenoxicam, phenylbutazone, and oxyphenthatrazone), nabumetone, gold compounds (such as auranofin, aurothioglucose, gold sodium thiomalate); immunosuppressive (such as cyclosporine, tacrolimus (FK-506), sirolimus (rapamycin), azathioprine, mycophenolate mofetil); angiogenic such as vascular endothelial growth factor (VEGF), fibroblast growth factor (FGF); nitric oxide donors; anti-sense oligo nucleotides and combinations thereof.

The method includes obtaining an image of the living tissue by photoacoustic imaging. In various embodiments, obtaining an image of the living tissue by photoacoustic imaging comprises obtaining an image of the living tissue by at least one of photoacoustic tomography or multispectral optacoustic tomographic imaging.

In some embodiments, obtaining an image of the living tissue by photoacoustic imaging comprises obtaining an image of the living tissue by photoacoustic tomography.

Generally, photoacoustic tomography is based on reconstruction of an internal photoacoustic source distribution, from measurements acquired by scanning ultrasound detectors over a surface that encloses the source under study. In use, each temporal photoacoustic signal, measured at various detection positions, provides one-dimensional radial information about the photoacoustic source relative to the detector position, while a two-dimensional surface scans offer other two-dimensional lateral information about the photoacoustic source. Combining the temporal and spatial measurements provides information for a reconstruction of a three-dimensional photoacoustic source.

In some embodiments, obtaining an image of the living tissue by photoacoustic imaging comprises obtaining an image of the living tissue by multispectral optacoustic tomographic imaging (MSOT).

MSOT operates through several millimeters to centimeters of tissue to enable tomographic three-dimensional imaging with optical contrast, which is significantly deeper than that of microscopy. In use, pulsed light of time-shared multiple wavelengths illuminates the tissue of interest and establishes transient photon fields in tissue. In response to the fast absorption transients by tissue elements, acoustic responses may be generated via the photoacoustic phenomenon, which may then be detected with acoustic detectors. By modeling photon and acoustic propagation in tissues and using inversion methods, images may be generated and spectrally unmixed to yield biodistribution of reporter molecules and tissue biomarkers. Light of different wavelengths may be selected to target absorption transient of the chromophore or fluorochrome selected for spectral differentiation.

The photoacoustic imaging may be a laser-based photoacoustic imaging. The photoacoustic imaging may be carried out at a wavelength in the range of about 400 nm to about 900 nm, which correspond to the visible range (400 nm to 750 nm) and near infrared region of the spectrum (750 nm to 900 nm).

In various embodiments, obtaining an image of the living tissue by multispectral optacoustic tomographic imaging include carrying out the imaging at a wavelength in the range of about 680 nm to about 980 nm.

Obtaining an image of the living tissue may be carried out in vivo or in vitro. In some embodiments, obtaining an image of the living tissue is carried out in vivo. In other embodiments, the living tissue is contained in a sample, and obtaining an image of the living tissue is carried out in vitro.

Various embodiments refer in a further aspect to use of a photoacoustic contrast agent comprising or consisting of a photosensitizer in photoacoustic imaging. Examples of suitable photosensitizers that may be used have already been discussed above.

In various embodiments, the photosensitizer is selected from the group consisting of a second generation porphyrin-based photosensitizer, a non-porphyrin-based photosensitizer, and combinations thereof. For example, the photosensitizer may be selected from the group consisting of zinc pthalocyanine, methylene blue, 2,4-bis[4-(N,N-dibenzylamino)-2,6-dihydroxyphenyl]squaraine, protoporphyrin IX, chlorin e6, and combinations thereof.

In specific embodiments, the photosensitizer comprises or consists of zinc pthalocyanine.

In various embodiments, the photoacoustic imaging is photoacoustic microscopy. For example, the photoacoustic microscopy may include laser pulse generation, delivery of the laser pulse to a subject under study, reception of photoacoustic signal generated from the subject, image reconstruction, and display of the image. Exemplary illustrations of how photoacoustic microscopy may be carried out are provided in the examples disclosed herein.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, lengths and sizes of layers and regions may be exaggerated for clarity.

As used herein, the term "and/or" includes any and all combinations of one or more of the associated listed items. The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Photoacoustic imaging is a novel hybrid imaging modality combining the high spatial resolution of optical imaging with the high penetration depth of ultrasound imaging. Here, for the first time, efficacy of various photosensitizers, which may be used as photodynamic therapeutic (PDT) agents, were investigated for the first time as photoacoustic contrast agents.

Photoacoustic imaging of photosensitizers exhibits advantages over fluorescence imaging, which is prone to photobleaching and autofluorescence interference. In this work, photoacoustic activity of 5 photosensitizers: zinc phthalocyanine, protoporphyrin IX, 2,4-bis[4-(N,N-dibenzylamino)-2,6-dihydroxyphenyl]squaraine, chlorin e6 and methylene blue in phantoms were investigated, among which zinc phthalocyanine showed the highest photoacoustic activity.

Chemical formula of zinc phthalocyanine, protoporphyrin IX, 2,4-bis[4-(N,N-dibenzylamino)-2,6-dihydroxyphenyl] squaraine, chlorin e6 and methylene blue are respectively

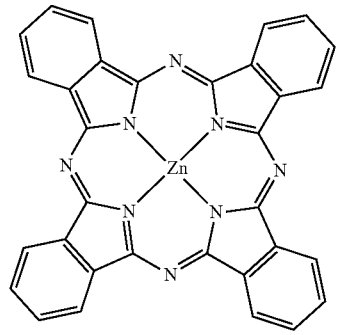

zinc phthalocyanine

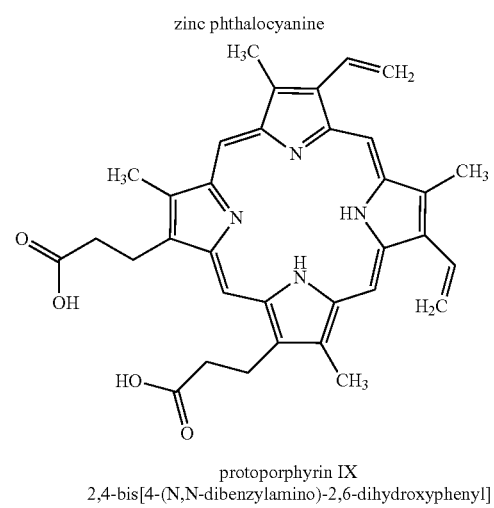

protoporphyrin IX
2,4-bis[4-(N,N-dibenzylamino)-2,6-dihydroxyphenyl]

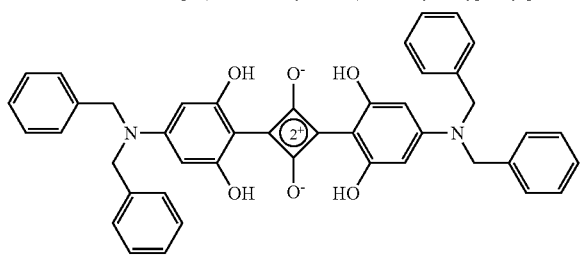

squaraine

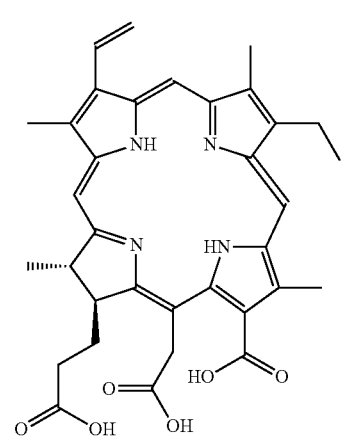

chlorin e6 methylene blue:

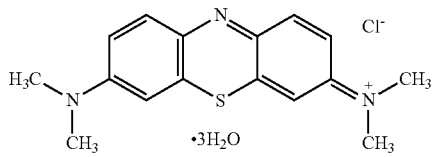

Subsequently, using zinc phthalocyanine, tumor localization efficiency and biodistribution at multiple time points in a murine model were investigated using photoacoustic imaging. It was observed that the probe localized at the tumor within 10 minutes post injection, reaching peak accumulation around 1 hour and was cleared within 24 hours, thus, demonstrating the potential of photosensitizers as photoacoustic imaging contrast agents in vivo. This means that advantages of photosensitizers such as preferential tumor uptake and PDT efficacy may be combined with photoacoustic imaging capabilities to achieve longitudinal monitoring of cancer progression and therapy in vivo.

Example 1

Preparation of PA Contrast Agents

Zinc Pthalocyanine, Protoporphyrin IX, Methylene Blue and 2,4-bis[4-(N,N-dibenzylamino)-2,6-dihydroxyphenyl] squaraine in powder form were purchased from Sigma-Aldrich. Chlorin e6 was purchased from Frontier Scientific (Logan, Utah). Stock solutions of all compounds were prepared in dimethyl sulfoxide (DMSO). Formulations for absorbance measurements and animal studies were made in 10% DMSO.

Example 2

UV Absorbance Measurement

In order to obtain information about optical absorption properties of the contrast agents, their wavelength-dependent absorption spectra at known concentrations were measured using a spectrophotometer.

In the experiments carried out, wavelength-dependent absorption spectrum of the contrast agents was measured from 680 nm to 900 nm using a spectrophotometer (DU 730, Beckman Coulter), which in turn was used as an input spectrum for multispectral post-processing of photoacoustic signals.

The spectra were normalized to obtain the concentration-independent normalized absorbance (directly proportional to extinction coefficient) as a function of wavelength for each contrast agent (FIG. 1), based on Beer-Lambert law:

$$A(\lambda) = \ln(I_0/I) = \varepsilon(\lambda) c l$$

where $A(\lambda)$ is the measured wavelength-dependent absorbance, $I_0$ is the incident light intensity, $I$ is the transmitted light intensity, $\varepsilon(\lambda)$ is the wavelength-dependent extinction coefficient of the contrast agent, $c$ is the concentration of the contrast agent and $l$ is the path length of the quartz cuvette (1 cm).

As shown in FIG. 1, all the studied contrast agents exhibit a general decreasing trend in absorbance with increasing wavelength in the near infrared (NIR) range from 680 nm to 900 nm, in which ZnPc shows the highest overall absorbance, followed by MB, Sq, PPIX and Ce6 in decreasing order.

Although these probes have higher reported molar extinction coefficients in the visible light range of the electromagnetic spectrum, and hence, are expected to provide stronger PA signals at these wavelengths, PA activity of these compounds in the NIR region from 680 nm to 900 nm was studied, because at these wavelengths there is lower tissue absorption enabling imaging at greater depths. At wavelengths above 900 nm, water absorption increases significantly, making the 680 nm to 900 nm range optimal for in vivo deep tissue imaging.

Example 3

MSOT Experimental Parameters and Protocol

In order to verify the PA activity of the photosensitizers under controlled conditions, phantom measurements for all the contrast agents were performed, in the 680-900 nm wavelength range, each at 5 different concentrations.

All phantom and in vivo mouse imaging experiments were performed using a real-time multispectral optacoustic tomographic (MSOT) imaging system; inVision 128 (iThera Medical GmbH, Neuherberg, Germany).

Figure 2A:
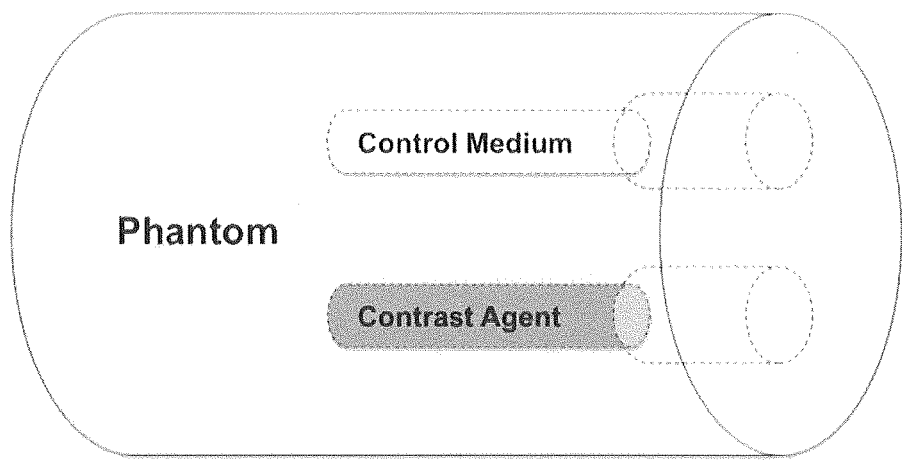
FIG. 2A is a schematic diagram showing the phantom used in the experiments.
Figure 2B:
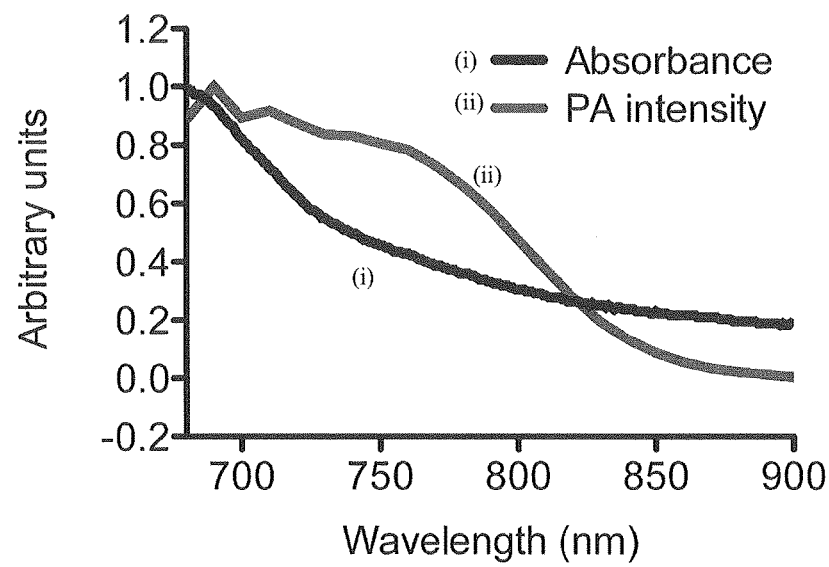
FIG. 2B to 2F are graphs showing (i) normalized absorbance, and (ii) PA intensity as a function of wavelength for (B) zinc pthalocyanine; (C) protoporphyrin IX; (D) 2,4-bis[4-(N,N-dibenzylamino)-2,6-dihydroxyphenyl]squaraine; (E) chlorin e6; and (F) methylene blue.
Figure 2C:
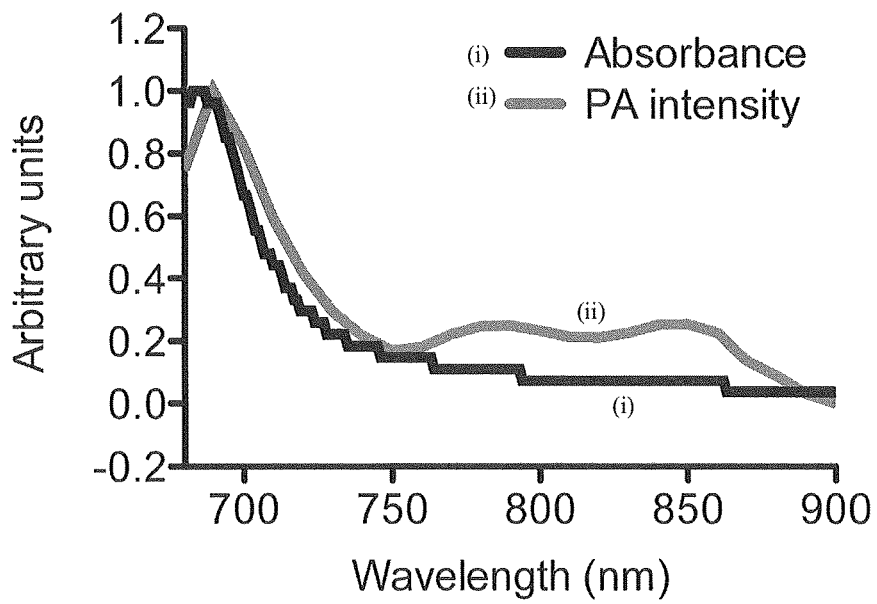
Figure 2D:
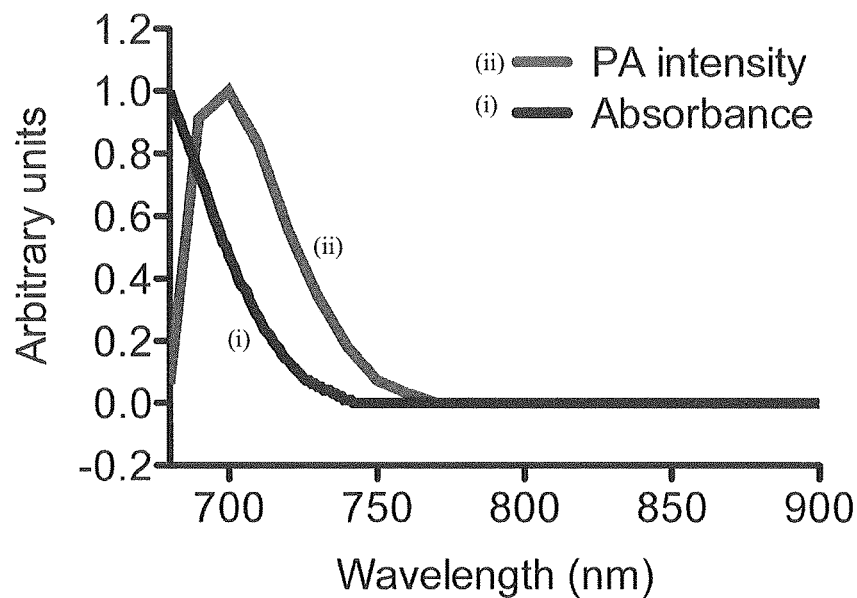
Figure 2E:
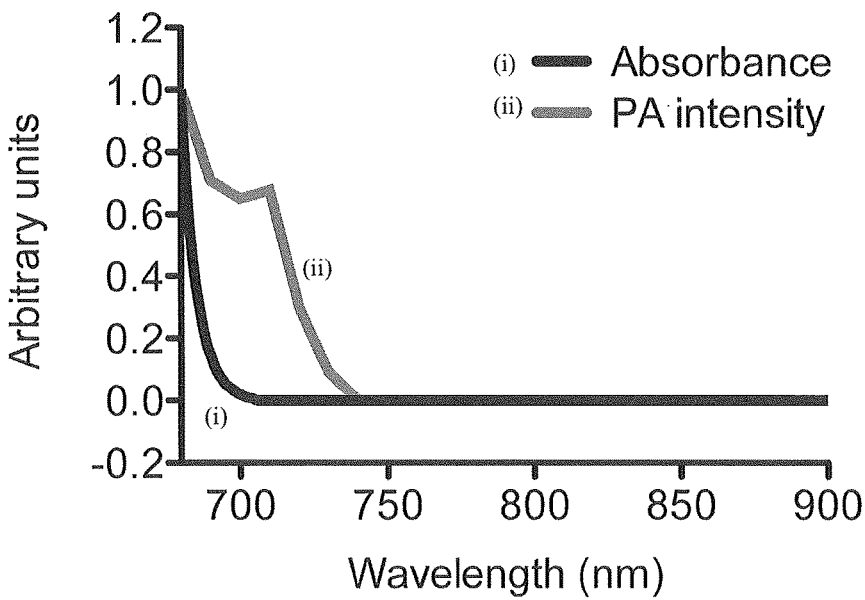
Figure 2F:
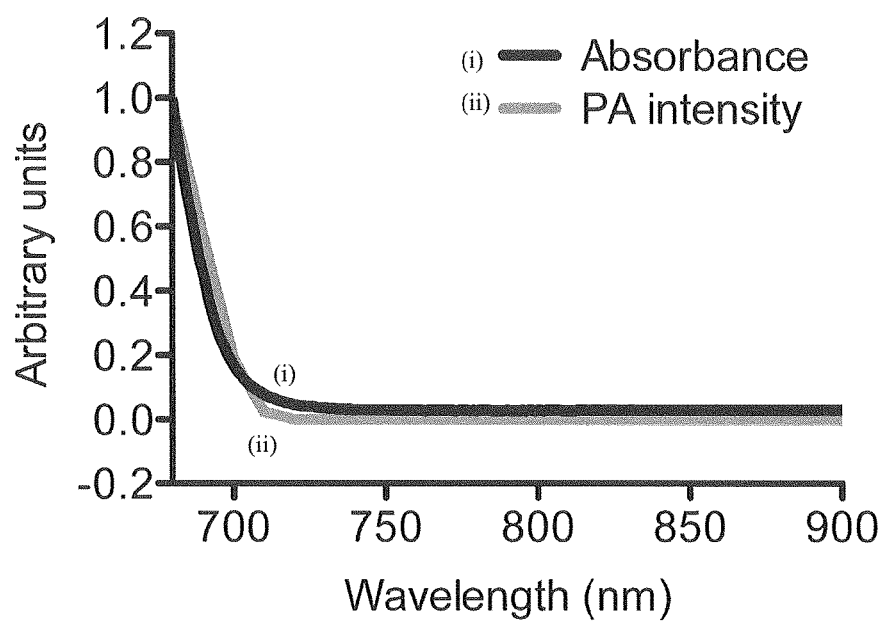

The phantom was made of polyurethane, cylindrical in shape with a diameter of 2 cm, which was specially designed to mimic the shape, size and optical properties of the mouse (iThera Medical GmbH, Neuherberg, Germany). In addition, it had 2 inner cylindrical channels, each with diameter of 3 mm, one for holding the control medium and the other for holding the dissolved contrast agent in the same medium, to measure PA signal compared to the control medium, as shown in FIG. 2A.

Optical excitation was provided by an optical parametric oscillator (OPO) with a tunable near infra-red (NIR) wavelength range from 680 nm to 980 nm, which is in turn pumped by a Q-switched Nd:YAG laser with a pulse duration of 10 ns and repetition rate of 10 Hz. Light was delivered by a fiber bundle divided into 10 output arms to illuminate the sample from multiple angles around the imaging plane.

Photoacoustic (PA) signals were acquired using a 128-element concave transducer array spanning a circular arc of 270°. This transducer array had a central frequency of 5 MHz, which provided a transverse spatial resolution in the range of 150 µm to 200 µm. One transverse image slice was acquired from each laser pulse, resulting in a frame-rate of 10 Hz.

During image acquisition, the sample is translated through the transducer array along its axis across the volume ROI, in order to capture the corresponding transverse image slices. Data from multiple transverse slices across the channel portion which contains the probe and control were recorded. Excitation wavelength scan from 680 to 900 nm with an interval of 10 nm for each transverse slice was applied, and the averaged PA signals from 10 frames for each wavelength and position were recorded.

After image reconstruction, results showed that all the contrast agents exhibit wavelength dependent PA activity in phantoms. In addition, there is a similar trend in waveform between absorbance and PA intensity (both normalized) as a function of wavelength for all the contrast agents, with a peak at around 680 nm to 700 nm for both absorbance and PA intensity, which tapered downwards towards longer wavelengths. This demonstrated a strong correlation between optical absorption spectra and the PA spectra, which validates our data, as shown in FIG. 2B to FIG. 2F.

In PA imaging, PA intensity induced by optical absorption is proportional to light energy deposition, which is the product of the absorption coefficient and the local light fluence. Thus, the small deviations in trend between absorbance and PA intensities may be attributed to light fluence changes caused by slight variations in laser intensity.

In addition, PA signal for each contrast agent was spectrally unmixed via linear regression. This allowed isolation of the individual contribution of the contrast agent of interest that may be plotted as a function of concentration, which in turn was used to produce a straight line of best fit based on least-squares regression, for each contrast agent.

Figure 3:
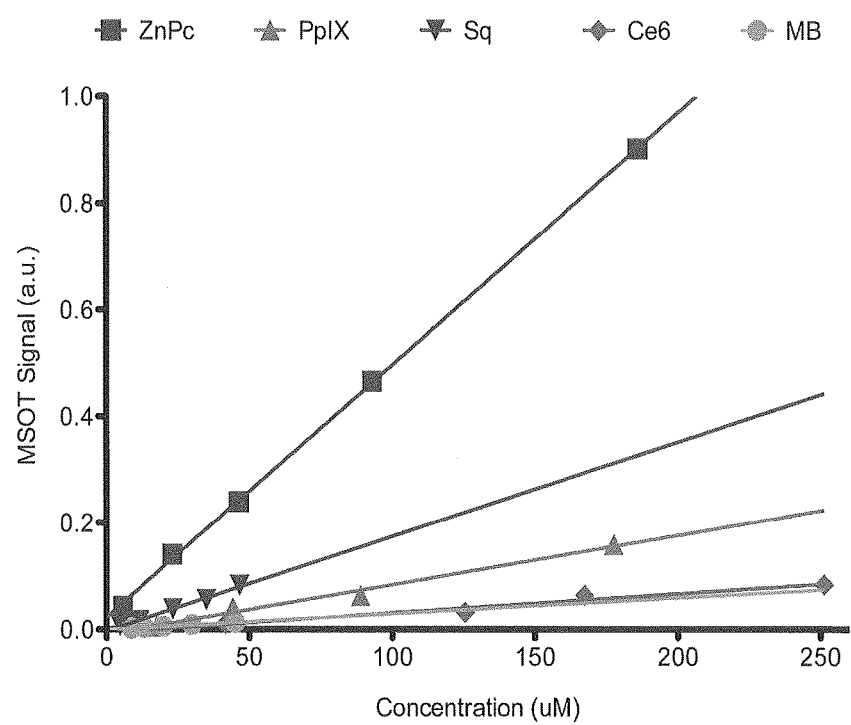
FIG. 3 is a graph showing multispectrally unmixed PA signal intensity as a function of concentration with a line of best fit for each contrast agent.
Figure 4A:
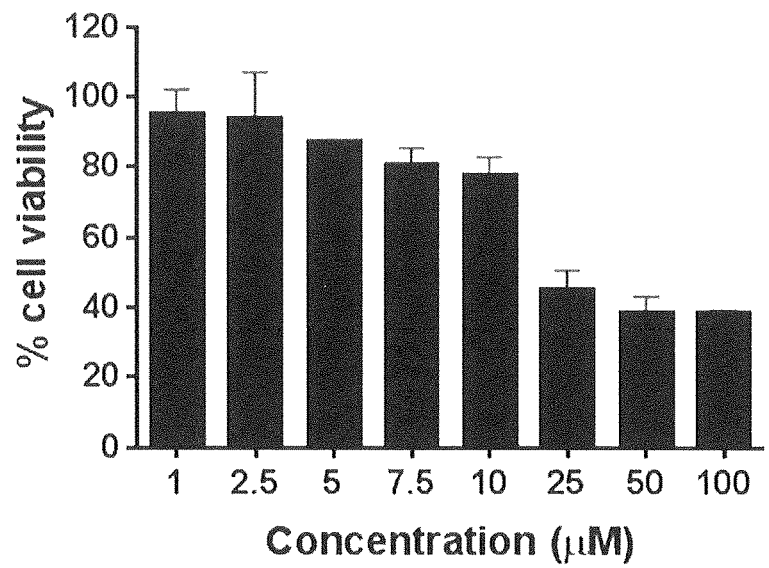
FIG. 4A to 4E are graphs depicting dark toxicity of the photosensitizers on oral squamous carcinoma cells (OSCC) for (A) zinc pthalocyanine; (B) protoporphyrin IX, (C) 2,4-bis[4-(N,N-dibenzylamino)-2,6-dihydroxyphenyl] squaraine, (D) chlorin e6, and (E) methylene blue. OSCC cells were exposed to varying concentrations (1 µM to 100 µM) of all five photosensitizers for 24 hours in dark and measured for cell viability using Cell Counting Kit-8 (CCK-8, Sigma-Aldrich). Cells treated with protoporphyrin IX (PPIX) and methylene blue (MB) exhibited more than 50% cell viability even up to 100 µM concentrations. While cells treated with chlorin e6 (Ce6) exhibited more than 50% viability up to 50 µM, those treated with zinc pthalocyanine (ZnPc) and sqauraine (Sq) exhibited more than 50% viability up to 10 µM concentration.
Figure 4B:
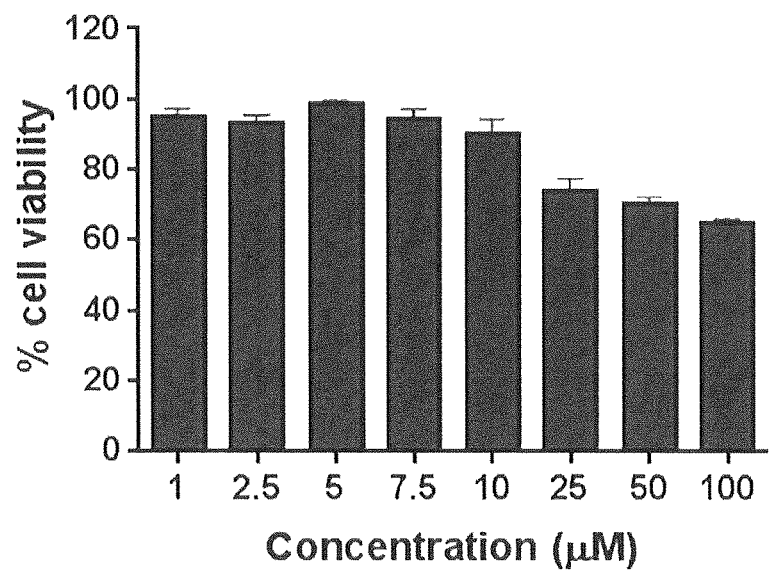
Figure 4C:
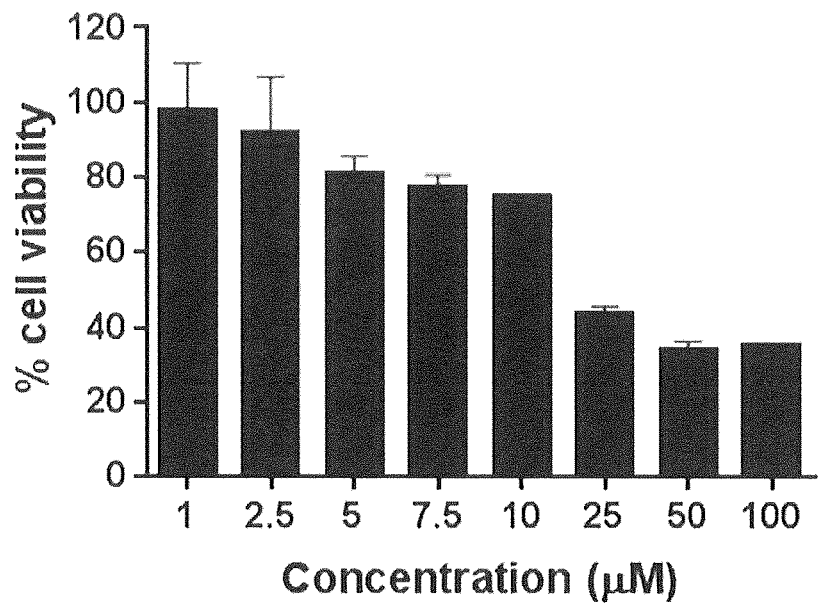
Figure 4D:
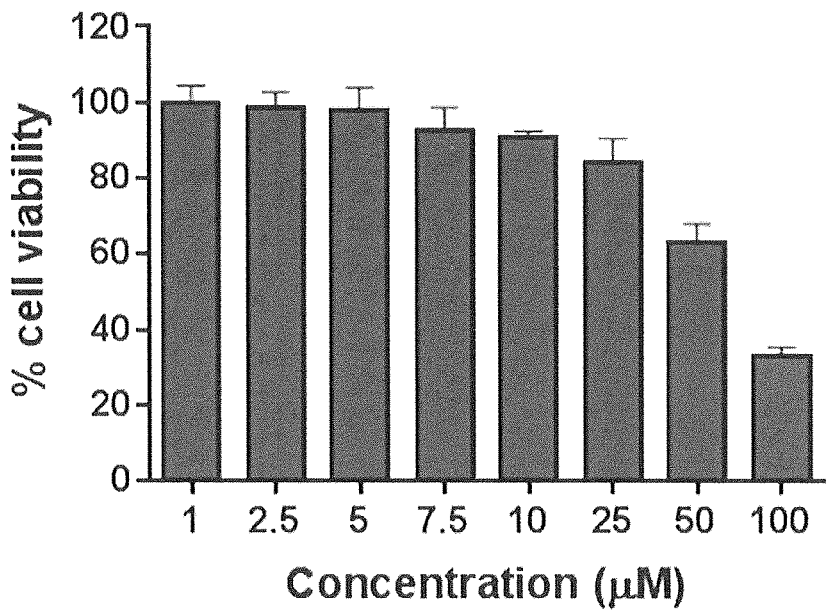
Figure 4E:
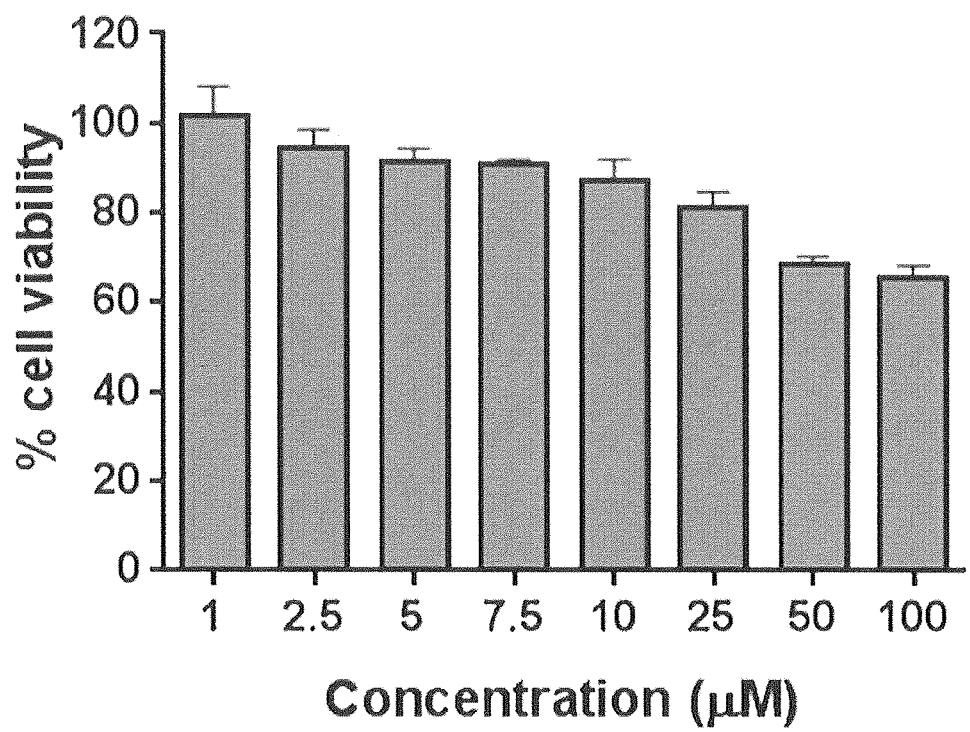
Figure 5:
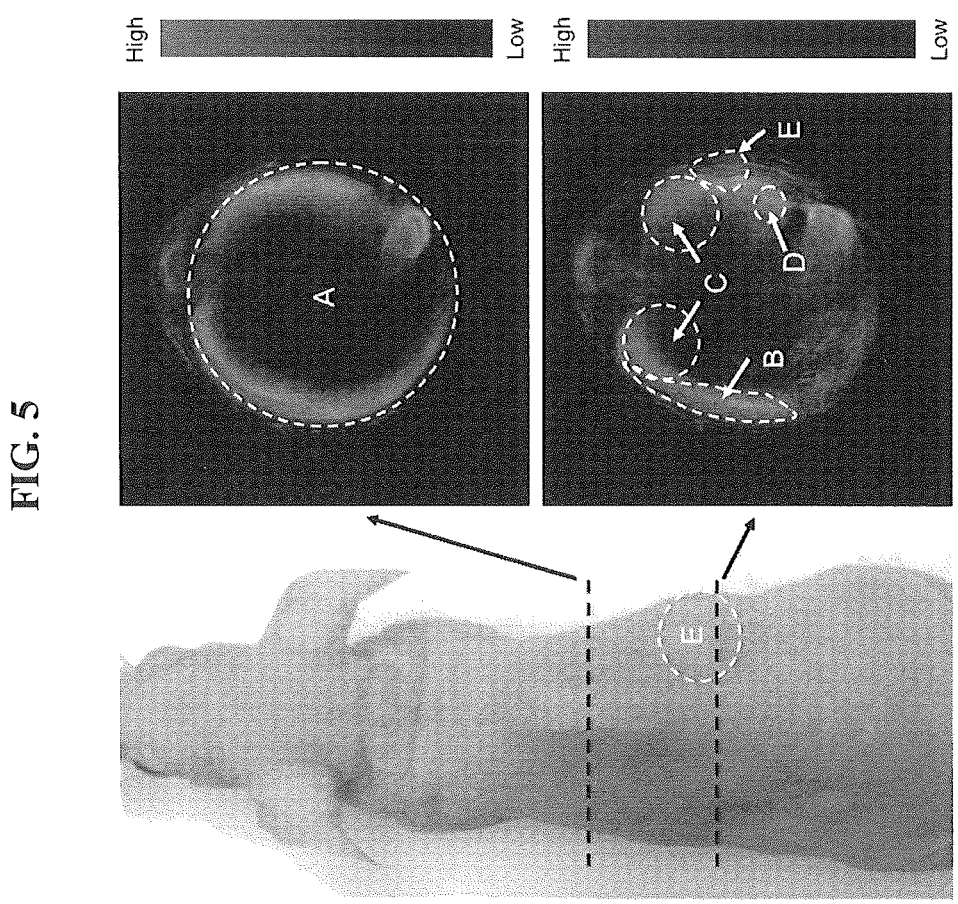
FIG. 5 shows a picture of mouse with tumor on right flank, with an upper transverse slice through the liver region and a lower slice through the lower abdomen (black dotted). In vivo PA images of corresponding transverse slices through the mouse at 1 hr post injection, showing probe biodistribution (middle column), oxy- (red) and deoxy-haemoglobin (blue) concentrations (right column) within the (A) liver, (B) spleen, (C) kidneys, (D) intestines, and at the (E) tumor site. The oxyhaemoglobin distribution is highly spatially correlated with the probe distribution.

As shown in FIG. 3, the line corresponding to ZnPc had the highest gradient, which corresponded to the highest increase in PA signal for an incremental increase in concentration, when compared to the rest. This gradient was thereby defined by the inventors as a form of relative PA quantum yield ($\phi P$), a kind of measure of the efficiency of the conversion of light absorption into photoacoustic signal. This is analogous to fluorescence quantum yield ($\phi$), which measures efficiency of the conversion of light absorption into fluorescence emission.

Relative $\phi$ of the 5 compounds were computed and listed in TABLE 1. The numbers shown are not absolute values, but arbitrary ratios, which reflect the relative PA strength of one compound against that of another.

TABLE 1

Fluorescence, singlet oxygen, and relative PA quantum yields of various photosensitizers.

| Photosensitizers | Fluorescence Quantum Yield ($\phi F$) | Singlet Oxygen Quantum Yield ($\phi \Delta$) | Relative PA Quantum yield ($\phi P$) |
|---|---|---|---|
| ZnPc | 0.06 [23] | 0.62 [23] | 0.47 |
| PpIX | 0.16 [23] | 0.56 [23] | 0.093 |
| Sq | 0.037 [27] | 0.61-0.74 [28] | 0.18 |
| Ce6 | 0.19 [23] | 0.65 [23] | 0.036 |
| MB | 0.02 [23] | 0.55 [23] | 0.029 |

References Referred to TABLE 1:
Ref. [23]: Lovell, J. F., Liu, T. W. B., Chen, J. & Zheng, G. Activatable photosensitizers for imaging and therapy. Chem. Rev. 110, 2839-2857 (2010).
Ref. [27]: Kamat, P. V. et al. Excited-state properties and photosensitization behaviour of bis(2,4-dihydroxyphenyl) squaraine. J. Chem. Soc., Faraday Trans. 89, 2397-2402 (1993).
Ref. [28]: Yano, S. et al. Current states and future views in photodynamic therapy. J. Photochem. Photobiol. C: Photochem. Rev. 12, 46-67 (2011).

As shown in TABLE 1, it was reported that these photosensitizers have low fluorescence quantum yields (less than 0.2) but reasonably high singlet oxygen quantum yields (about 0.5). This means that although these photosensitizers were able to offer high PDT efficacy, they exhibit low fluorescence, which may not be adequate for high contrast diagnostic imaging. However, this limitation can be circumvented by using PA imaging, as shown in this work.

Moreover, on testing these compounds for dark toxicity on oral squamous carcinoma cell line (OSCC) for varying concentrations (1 to 100 μM), they exhibited more than 50% cell viability for concentrations up to 100 μM of PPIX and MB, 50 μM of Ce6 and 10 μM of Sq and ZnPc (FIG. 4). This vast range of concentrations tested was inclusive of the in vivo dose range for photodynamic therapy for most of them (see TABLE 2) thus making a point that they may be used as PA imaging contrast agents at concentrations that do not induce much toxicity in vivo.

TABLE 2

Pre-clinical in vivo dose of the various photosensitizers used on mice (from literature). Concentration of drug in the blood was calculated on the assumption that volume of blood in mice was 2 ml.

| Photosensitizers | Dose mg/kg body weight | Concentration of drug in the blood (μM) |
|---|---|---|
| ZnPc | 0.21 [1] | 3.63 |
| PpIX | 2 [2] | 88.88 |
| Sq | 12.5 [3] | 181.40 |
| Ce6 | 0.5 [4] | 41.90 |
| MB | 50 [5] | 1337.00 |

References Referred to TABLE 2:
Ref. [1]: van Leengoed, H. L. L. M., Cuomo, V., Versteeg, A. A. C., van der Veen, N., Jori, G. & W. M. Star. In vivo fluorescence and photodynamic activity of zinc phthalocyanine administered in liposomes. Br. J. Cancer. 69, 840-845 (1994).
Ref. [2]: Koo, H. et al. In vivo tumor diagnosis and photodynamic therapy via tumoral pH-responsive polymeric micelles. 46(31):5668-70 (2010).
Ref. [3]: Avirah, R. R., Jayaram, D. T., Nagappanpillai, A. & Ramaiah, D. Squaraine dyes in PDT: from basic design to in vivo demonstration. Org. Biomol. Chem. 10, 911 (2012).
Ref. [4]: Shim, G., Lee, S., Kim, Y. B., Kim, C. W. & Oh, Y. Enhanced tumor localization and retention of chlorin e6 in cationic nanolipoplexes potentiate the tumor ablation effects of photodynamic therapy. Nanotechnology. 22, 365101 (8pp) (2011).
Ref. [5]: Chen, Y., Zheng, W., Li, Y., Zhong, Y., Ji, J. & Shen, P. Apoptosis induced by methylene-blue-mediated photodynamic therapy in melanomas and the involvement of mitochondrial dysfunction revealed by proteomics. Cancer Sci. 99 (10):2019-27 (2008).

For in vivo imaging, ultrasound gel was applied on the mouse skin surface, and measurements were recorded in temperature-controlled water for good acoustic coupling. An animal holder with a thin polyethylene membrane was used to prevent direct contact between the mouse and the water.

Example 4

Animal Preparation

All animal experimental procedures were performed in accordance with the protocol #120774 approved by the Institutional Animal Care and Use Committee (IACUC).

Xenograft mice models were established by injecting subcutaneously into the right flank of mouse, 0.2 mL of cell suspension containing about $5 \times 10^6$ to $6 \times 10^6$ MCF-7, a human metastatic breast cancer cell line or OSCC, a human oral squamous carcinoma cell line and matrigel (BD biosciences) in 1:1 volume ratio. When the tumor volume reached a palpable size, the mouse was used for in vivo PA imaging.

Example 5

In Vivo Longitudinal Monitoring of Probe Biodistribution in Mouse Xenograft Model Based on the prioritization of the different photosensitizers for MSOT imaging by phantom analysis, ZnPc was evaluated in vivo, as it was found to have the strongest PA signal in phantoms.

ZnPc at a dosage of 0.21 mg/kg was injected via a catheter into the tail vein of a subcutaneous tumor bearing mice anaesthetized under isoflurane and the probe biodistribution or uptake was monitored over time in various organs of liver, spleen, kidneys, intestines and tumor using photoacoustic imaging. Before image acquisition, a volume ROI consisting of transverse slices with a step size of 0.3 mm spanning from the liver to the lower abdomen was selected by manual inspection of live MSOT images, and the 6 laser excitation wavelengths of 680, 700, 750, 800, 850 and 900 nm were selected for correspondence with the major turning points in the absorption spectra of ZnPc, oxy-haemoglobin and deoxy-haemoglobin. Multispectral imaging was then performed with 10 signal averages per wavelength per transverse slice, before injection, during injection and 1, 3, 5, and 24 hr post-injection.

Example 6

Image Reconstruction and Multispectral Processing

Images were reconstructed using a model-based approach as discussed in Rosenthal, A. et al. (Rosenthal, A. et al., *Fast semi-analytical model-based acoustic inversion for quantitative optoacoustic tomography. IEEE Trans. Med. Imag.* 29, 1275-1285 (2010)) for offline analysis. After image reconstruction, spectral unmixing was performed to resolve individual components from different chromophores in the system. For each pixel in the image, the method fits the total measured optoacoustic spectrum to the known absorption spectra of the individual chromophores, based on least-squares linear regression.

Example 7

Image Processing

A volume ROI consisting of transverse slices spanning from the liver to the lower abdomen was scanned, and maximum intensity projections (MIPs) based on these slices were constructed for image analysis.

Figure 6A:
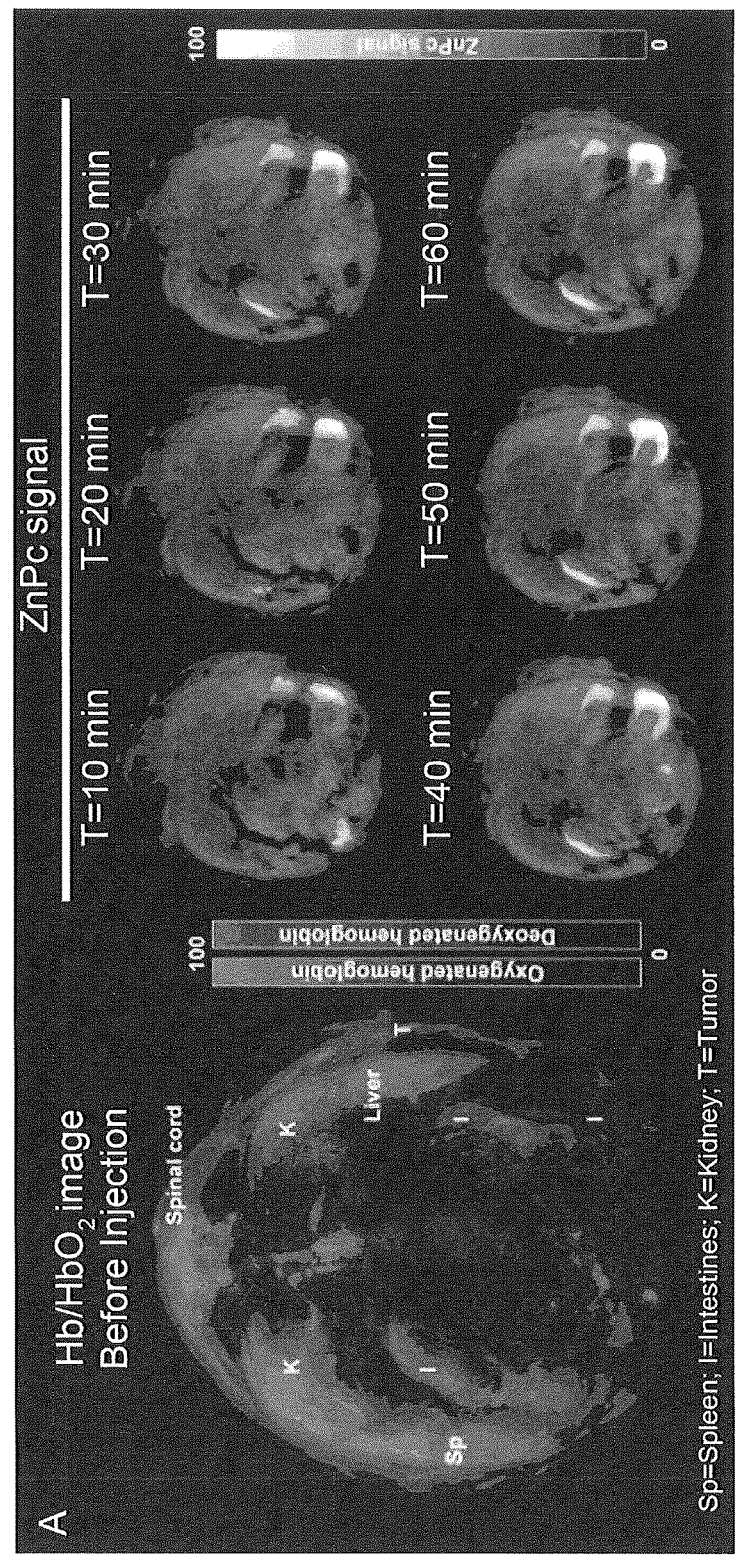
FIG. 6A shows in vivo background-corrected maximum intensity projection (MIP) images of transverse slices through mouse pre-injection, and within the first hour after injection, showing gradual probe accumulation within the tumor site (T) and various organs of spleen (Sp), intestines (I), kidney (K), and liver over time, at 10 min, 20 min, 30 min, 40 min, 50 min, and 60 min.
Figure 6B:
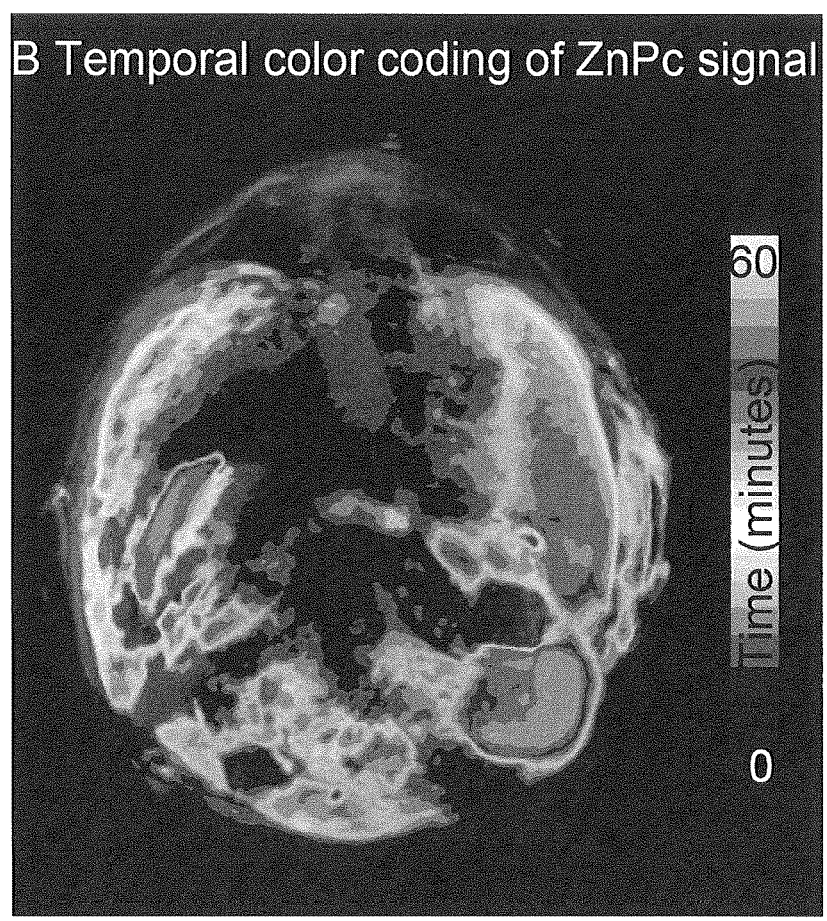
FIG. 6B shows time-resolved color coding of the multispectral optacoustic tomographic (MSOT) signal within the first hour after injection, demonstrating peak localization of probe at the tumor site and various organs at 1 hour post injection. A stack of MIPs of ZnPc signal over time (t=10 mins to 60 mins) is condensed in a parametric map visualizing the $t_{max}$ of ZnPc; peak concentrations of ZnPc are observed at t=60 mins.
Figure 7:
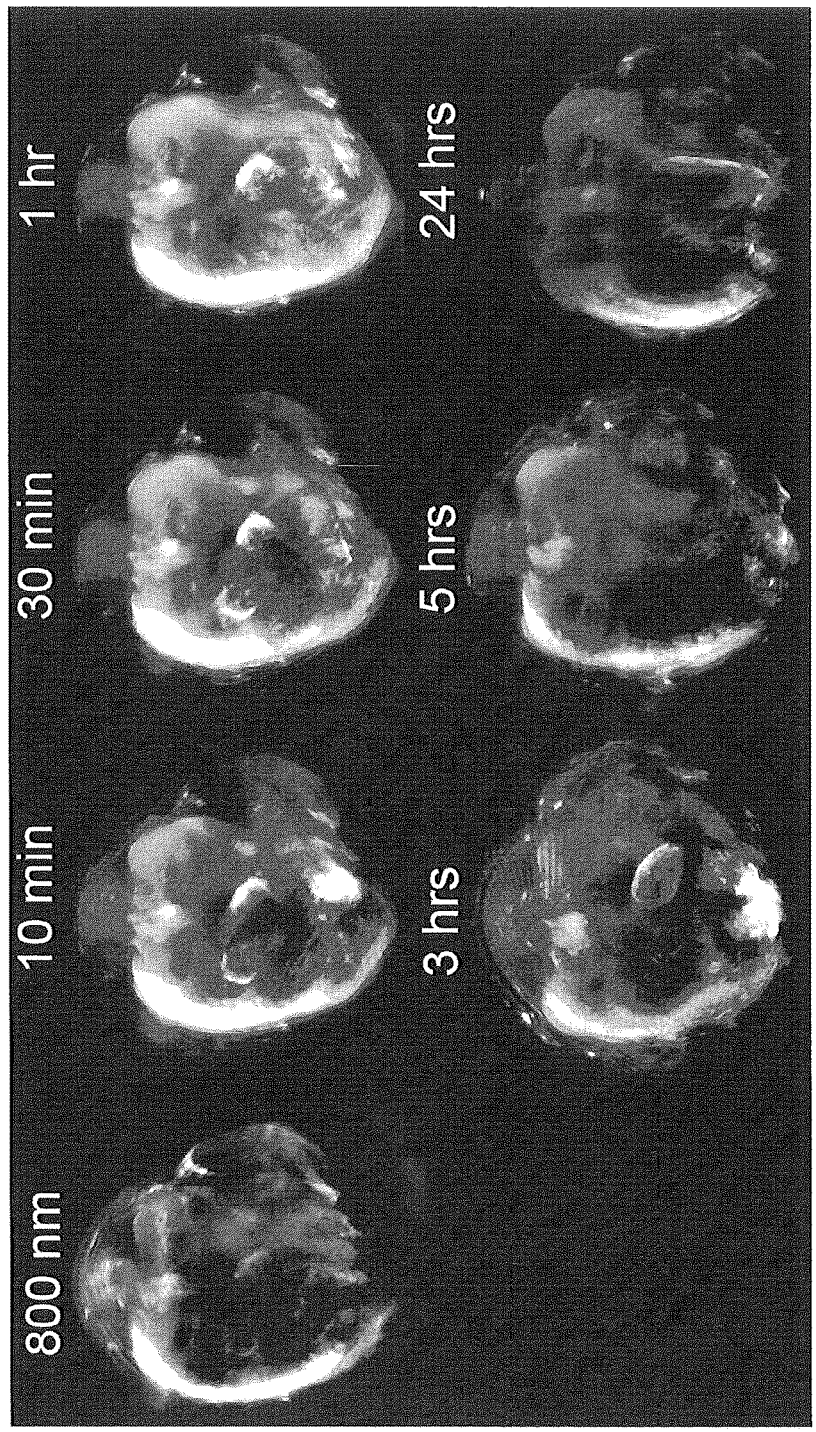
FIG. 7 shows in vivo non-background-corrected MIP images of transverse slices through mouse at various timepoints of 10 min, 30 min, 1 hr, 3 hrs, 5 hrs, and 24 hrs, post-injection, demonstrating strong probe MSOT signals within the liver, spleen, kidneys, intestines and tumor site. There is a gradual decrease in the tumor MSOT signal over time, which in turn implies probe clearance within a day.

Maximum intensity projection (MIP) images were prepared and presented in FIGS. 6 and 7, for better display of anatomy and quantification.

For the first hour in FIG. 6, the difference between the time-point images and the pre-scan image (before injection) were displayed, which was possible because the animal was intact and anaesthetized in the MSOT machine within the 1st hour. A strong in vivo MSOT signal of ZnPc was detected in the reticuloendothelial system (liver, spleen), intestines and tumor site within the first hour after injection, with peak accumulation at the 1-hour time point, as shown in the background-corrected images in FIG. 6.

For the later time points, this background subtraction was not possible, as the animal was removed and placed in the MSOT system repeatedly, with repositioning, in order to avoid overdosage of isoflurane for the entire 24-hour duration. Although FIG. 7 is not background-corrected, it still shows the biodistribution trend over the entire duration.

Figure 8A:
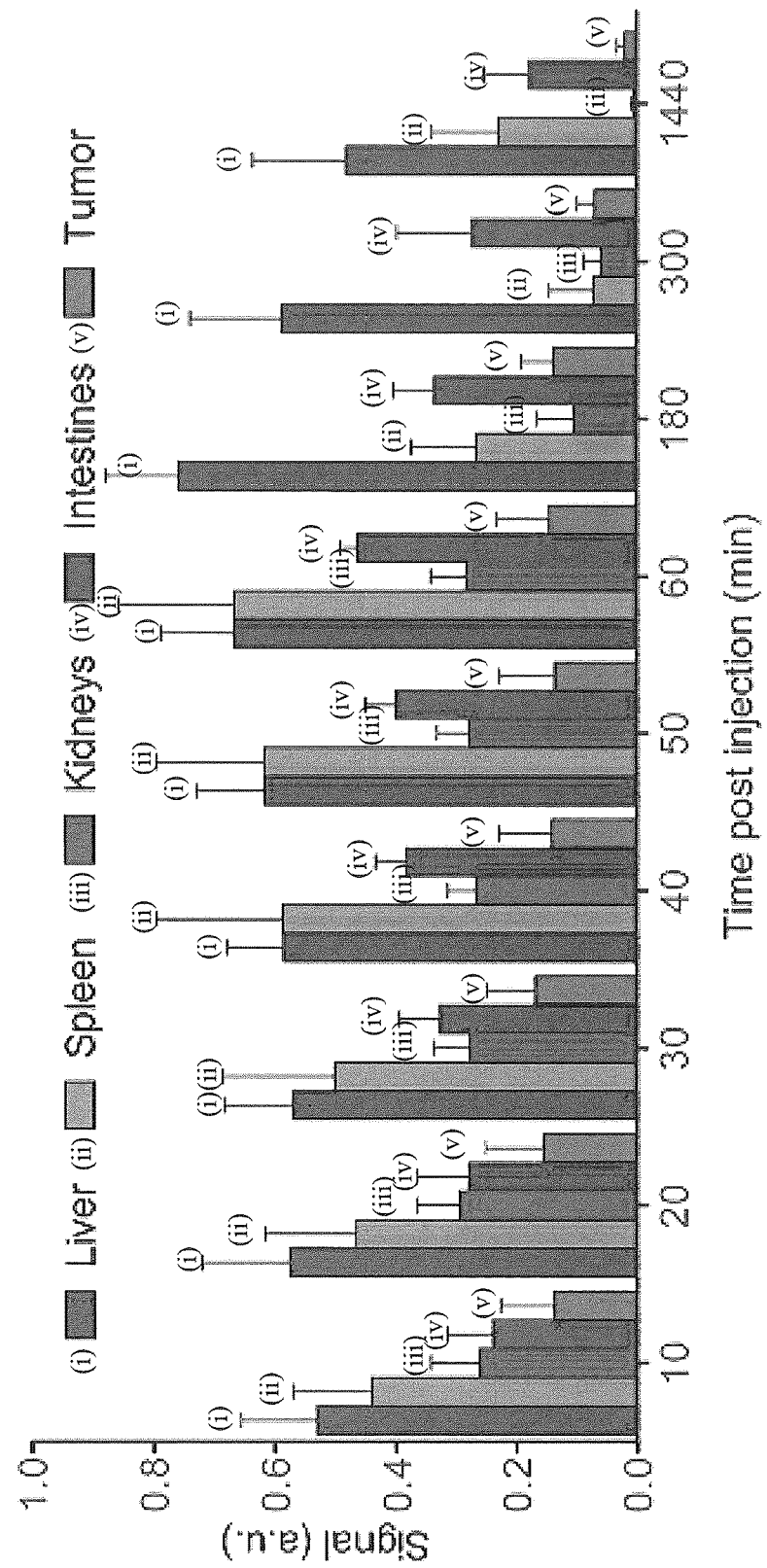
FIG. 8A is a graph showing biodistribution of ZnPc at various organs of (i) liver, (ii) spleen, (iii) kidneys, (iv) intestines, and (v) tumor at multiple time points. Y-axis: signal (a.u.); x-axis: time post injection (min).

Specifically, the non-background-corrected images in FIG. 7 and FIG. 8A showed that this signal gradually decreased in intensity beyond 1 hour up to a day, suggesting probe clearance within a day. This allowed for the rapid evaluation of PDT agent delivery after administration and may aid in optimizing photodynamic therapy time point planning. Apart from monitoring the accumulation in tumor, whole-body biodistribution of compounds may be visualized and quantified simultaneously by MSOT, which can aid in the elucidation of clearance pathways and choosing of optimal dosing strategies.

Figure 8B:
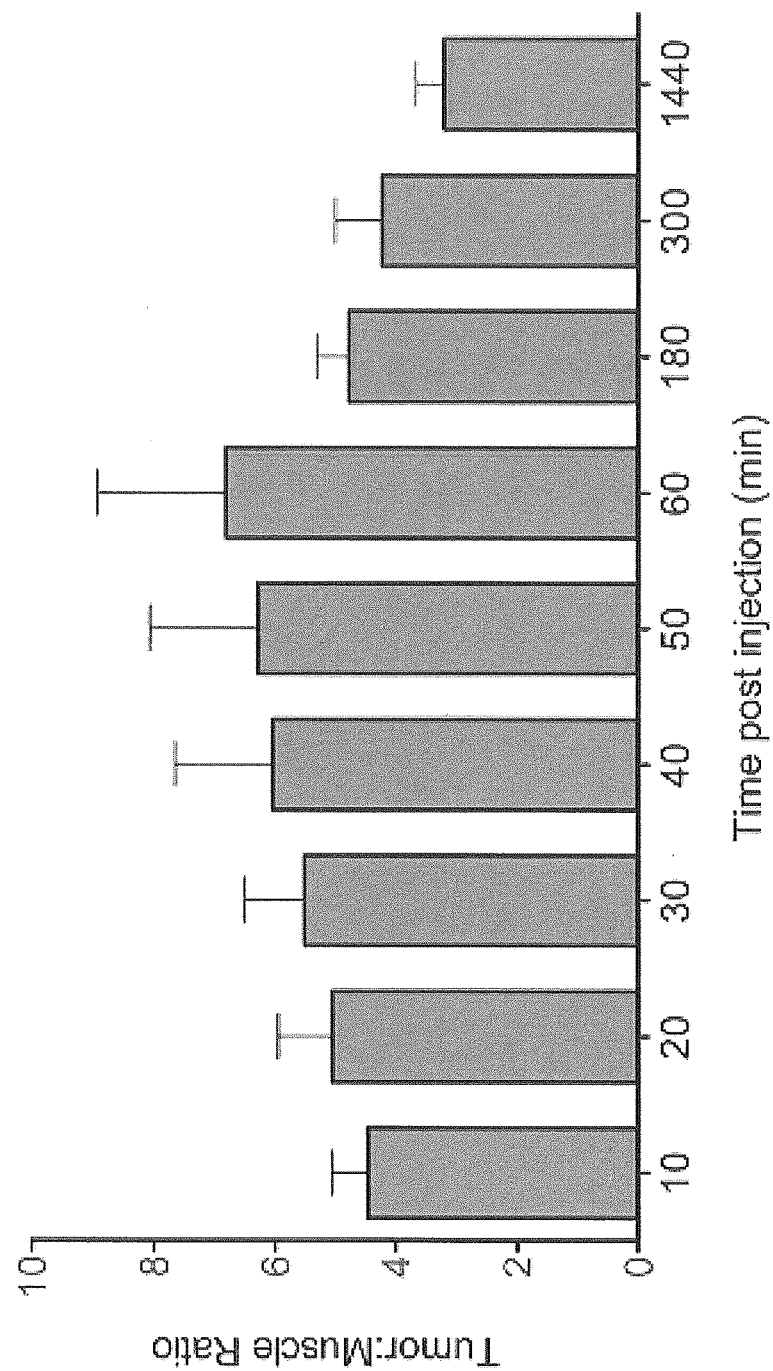
FIG. 8B is a graph showing tumor-to-muscle ratio of MSOT signals at multiple time points (n=4). Y-axis: tumor-to-muscle ratio; x-axis: time post injection (min) Tumor-to-muscle ratio of the MSOT signal peaks at 1-hour, thus making this time point ideal for photodynamic therapeutic (PDT) illumination and subsequent monitoring via MSOT imaging.

Without wishing to be bound by theory, it was hypothesized that ZnPc was most likely cleared through the hepatobiliary system, because high concentrations were found in the liver and intestines up to the 3-hour time point, whereas renal signal was much weaker in comparison, as shown in FIG. 7 and FIG. 8A. In addition, FIG. 8B also showed a peak tumor-to-muscle ratio of the MSOT signal at the 1-hour time point, making this time point ideal for PDT illumination and subsequent monitoring via MSOT imaging. Thus, in summary, the strong MSOT signals from ZnPc observed in the tumor region at the 1 hour time point suggested that MSOT imaging, combined with PDT, offers a novel theranostic approach with high translational potential.

As can be seen from the above, potential of five photosensitizers, namely zinc phthalocyanine (ZnPc), protoporphyrin IX (PpIX), 2,4-bis[4-(N,N-dibenzylamino)-2,6-dihydroxyphenyl]squaraine (Sq), chlorin e6 (Ce6) and methylene blue (MB), as PA contrast agents were investigated. Though not exhaustive, the photosensitizers are representative of the various categories of photosensitizers, many of which have been used in clinical trials. To the best of the inventors' knowledge, this is the first evaluation of the various classes of photosensitizers as potential PA contrast agents.

These photosensitizers exhibited low fluorescence quantum yields and thus may potentially possess high PA activity, since an excited system may either relax back to the ground state through fluorescence or thermally through internal conversion. Moreover, PA imaging of photosensitizers exhibits advantages over fluorescence imaging, which is prone to photobleaching and autofluorescence interference. In addition, as these PDT agents preferentially accumulate in tumor due to the enhanced permeation and retention (EPR) effect, they offer tumor-targeted PA imaging.

In the experiments carried out, PA performance of the five PDT agents in a scattering phantom was first investigated. Next, to demonstrate in vivo PA activity and tumor-targeting efficacy, ZnPc was injected intravenously into mice and the biodistribution monitored over time using PA imaging. In light of the unique advantages such as clinical relevance, passive tumor-targeting ability and high PA activity, these photosensitizer-based PA contrast agents offer great potential in cancer diagnosis and therapy, for example, for tracking footprints of cancer progression in vivo. A number of photosensitizers have already been clinically approved and used on patients, localizing at tumor sites with reasonable therapeutic efficacy While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method of imaging living tissue by multispectral optoacoustic tomographic imaging, the method comprising:
introducing a photoacoustic contrast agent consisting of a photosensitizer into living tissue, wherein the photosensitizer consists of protoporphyrin, chlorin, phthalocyanine, squarine, methylene blue, or combinations thereof;
irradiating the photosensitizer in the living tissue with electromagnetic radiation having an excitation wavelength ranging from about 680 nm to about 900 nm, wherein the photosensitizer absorbs the electromagnetic radiation to result in thermoelastic expansion of the photosensitizer;

generating a photoacoustic signal due to the thermoelastic expansion; and obtaining an image of the living tissue based on the photoacoustic signal.

2. The method according to claim 1, wherein the photosensitizer consists of zinc phthalocyanine, or methylene blue, or 2,4-bis [4-(N,N-dibenzylamino)-2,6-dihydroxyphenyl] squaraine, or protoporphyrin IX, or chlorin e6, or combinations thereof.

3. The method according to claim 1, wherein the photosensitizer is zinc phthalocyanine.

4. The method according to claim 1, wherein obtaining the image of the living tissue based on the photoacoustic signal is carried out in vivo.

5. The method according to claim 1, wherein the living tissue is contained in a sample, and obtaining the image of the living tissue based on the photoacoustic signal is carried out in vitro.

6. The method according to claim 1, wherein the photosensitizer is introduced into the living tissue at a concentration ranging from 1 to 100 µM.

\* \* \* \* \*